US012571050B2

(12) United States Patent
Balasubramanyam et al.

(10) Patent No.: US 12,571,050 B2
(45) Date of Patent: Mar. 10, 2026

(54) METHOD OF PREDICTING RESPONSE TO THERAPY BY ASSESSING TUMOR GENETIC HETEROGENEITY

(71) Applicant: Roche Sequencing Solutions, Inc., Pleasanton, CA (US)

(72) Inventors: Aarthi Balasubramanyam, Sunnyvale, CA (US); Christine Ju, Pleasanton, CA (US); Xiaoju Ma, San Carlos, CA (US); Thomas Muley, Heidelberg (DE); Felix Herth, Heidelberg (DE); Nalin Tikoo, San Ramon, CA (US); Birgit Wehnl, Munich (DE); Liu Xi, Fremont, CA (US); Stephanie J. Yaung, San Jose, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 0 days.

(21) Appl. No.: 16/969,172

(22) PCT Filed: Feb. 11, 2019

(86) PCT No.: PCT/EP2019/053250
§ 371 (c)(1),
(2) Date: Aug. 11, 2020

(87) PCT Pub. No.: WO2019/158460
PCT Pub. Date: Aug. 22, 2019

(65) Prior Publication Data
US 2020/0399711 A1     Dec. 24, 2020

Related U.S. Application Data

(60) Provisional application No. 62/630,195, filed on Feb. 13, 2018.

(51) Int. Cl.
*C12Q 1/68*          (2018.01)
*C12Q 1/6886*        (2018.01)

(52) U.S. Cl.
CPC ..... *C12Q 1/6886* (2013.01); *C12Q 2600/156* (2013.01); *C12Q 2600/158* (2013.01); *G01N 2800/54* (2013.01)

(58) Field of Classification Search
None
See application file for complete search history.

(56) References Cited

U.S. PATENT DOCUMENTS

2016/0115556 A1     4/2016   Erlander et al.

FOREIGN PATENT DOCUMENTS

| | | |
|---|---|---|
| CN | 106367490 A | 2/2017 |
| CN | 106498024 A | 3/2017 |
| KR | 20170125004 * | 11/2017 |
| WO | WO2013 A1 | 4/2013 |
| WO | WO2014151117 A1 | 9/2014 |
| WO | 2016/040901 A1 | 3/2016 |
| WO | WO2017123864 A1 | 7/2017 |

OTHER PUBLICATIONS

Baas et al; Curr Opin Oncol, vol. 23, pp. 140-149 2011.*
Wolpin et al; Gastroenterology, vol. 134, pp. 1296-1310, 2008.*
Anonymous, Abstract 5237: Monitoring minimal residual disease by urinary or plasma circulating tumor DNA of KRAS mutation burden in colorectal cancer patients with resectable liver metastases, Cancer Research, (2015), http://cancerres.aacrjournals.org/content/75/15_Supplement/5237.
Anonymous, Higher mutation burden and mutant allele fraction of circulating tumor DNA corresponds to worse progression free survival in metastatic breast cancer patients, Canc Res, (2017), http://cancerres.aacrjournals.org/content/78/4_Supplement/P2-02-18.
Goldberg, S et al., Early Assessment of Lung Cancer Immunotherapy Response via Circulating Tumor DNA, Clin Canc Res, (2018), pp. 1872-1880, vol. 24 Issue 8.
Gray, E et al., Circulating tumor DNA to monitor treatment response and detect acquired resistance in patients with metastatic melanoma, Oncotarget, (2015), pp. 42008-42018, vol. 6 Issue 39.
Hoffmann, F et al., Roche launches AVENIO ctDNA Analysis Kits for Oncology Research, India Pharma News, (2017), https://www.roche.com/dam/jcr:c6ecf4b7-6d24-48cb-8458-510ed0798625/en/med-cor-2017-05-08-e.pdf.
Kato, K et al., Numerical indices based on circulating tumor DNA for the evaluation of therapeutic response and disease progression in lung cancer patients, Scientific Reports, (2016), pp. 29093, vol. 6 Issue 1.
Newman, A et al., An ultrasensitive method for quantitating circulating tumor DNA with broad patient coverage, Nat Med, (2014), pp. 548-554, vol. 20 Issue 5.
Newman, A. M. et al, Integrated digital error suppression for improved detection of circulating tumor DNA, Nature Biotechnology, (2016), pp. 547-555, vol. 34, No. 5.
Sato, K et al., Individualized Mutation Detection in Circulating Tumor DNA for Monitoring Colorectal Tumor Burden Using a Cancer-Associated Gene Sequencing Panel, PLOS One, (2016), pp. e0146275, vol. 11 Issue 1.

* cited by examiner

*Primary Examiner* — Jehanne S Sitton
(74) *Attorney, Agent, or Firm* — Pamela C. Ancona

(57) ABSTRACT

The invention is a method of predicting response to therapy in a cancer patient by serial sampling the patient's cell-free tumor nucleic acids to determine a change in the number of mutations per amount of plasma.

1 Claim, 2 Drawing Sheets

HR, hazard ratio; mMMPM, mean mutant molecule counts per mL; PFS, progression-free survival CI, confidence interval; HR, hazard ratio; mMMPM, mean mutant molecule counts per mL; PFS, progression-free survival

METHOD OF PREDICTING RESPONSE TO THERAPY BY ASSESSING TUMOR GENETIC HETEROGENEITY

FIELD OF THE INVENTION

The invention relates to the field of oncology. More specifically, the invention relates to the field of nucleic acid-based testing of cancer patients.

BACKGROUND OF THE INVENTION

Despite routine use of chemoradiation therapy in many types of cancer, many patients have poor response or are refractory to treatment. The current prognostic methods are still limited to imaging. CT scans are typically performed a few months after treatment which may be too late to detect disease progression in patients who could have benefited from interim alternate therapies. CT scans also may not have sufficient resolution to accurately assess disease burden in patients with smaller tumors.

Circulating tumor DNA (ctDNA) in plasma is an alternative method to rapidly and accurately estimate disease burden, and can overcome biopsy site bias in the assessment of tumor clonality. ctDNA refers to fragmented DNA of tumor origin that is shed into the bloodstream. Prior analyses have indicated that ctDNA levels in plasma can be used as a tool for disease monitoring, can assess treatment response, and can detect residual and recurrent disease and treatment failure more quickly and accurately than CT scans Diehl F, et al. (2008) *Circulating mutant DNA to assess tumor dynamics.* Nat Med. September; 14(9):985-90. The prognostic value of ctDNA has been demonstrated in studies of several types of cancer. Almodovar K, et al. (2018) *Longitudinal cell-free DNA analysis in patients with small cell lung cancer reveals dynamic insights into treatment efficacy and disease relapse.* J Thorac Oncol. January; 13(1):112-123. Tie J. et al., (2015) *Circulating tumor DNA as an early marker of therapeutic response in patients with metastatic colorectal cancer.* Ann Oncol. 26:1715-1722. However, there is a need to transition from the qualitative assessment to a quantitative measurement that could guide patient care in real time.

SUMMARY OF THE INVENTION

The invention is a method of assessing and guiding a cancer patient's therapy by assessing the response to therapy by a non-invasive method. The method comprises measuring a change in a novel parameter associated with cell-free tumor DNA also known as circulating tumor DNA (ctDNA). The novel parameter measures the number of mutant ctDNA molecules per amount of blood plasma collected, e.g., per volume of plasma.

In one embodiment, the invention is a method of determining whether a cancer patient has positively responded to a therapy regimen, the method comprising the steps of: providing a blood plasma sample from the patient collected at a first time point during treatment regimen; providing a blood plasma sample from the patient collected at a second time point during treatment regimen; determining in the samples the sequence of at least a portion of each of the biomarkers listed in Table 1 or Table 2; determining in the samples the ratio of the number of mutations detected in the biomarkers to the volume of the samples (MMPM); and determining that the patient has responded to the therapy regimen if the MMPM in the second sample is lower than in the first sample; or determining that the patient has not responded to the therapy regimen if the MMPM in the second sample is not lower than in the first sample. The cancer may be selected from among non-small cell lung cancer (NSCLC), small cell lung cancer (SCLC) and colorectal cancer (CRC). The patient's response to therapy may be selected from increased progression free survival (PFS) and increased overall survival (OS). The therapy regimen may be selected from treatment with FOLFOXIRI-bevacizumab, treatment with FOLFOX-bevacizumab, capecitabine-bevacizumab and chemoradiation therapy. In some embodiments, the method further comprises collecting additional blood plasma sampled at additional time points during the treatment regimen and determining whether MMPM has decreased therein compared to the prior time point or is greater than MMPM in a subsequent time point.

In one embodiment, the invention is a method of treatment of a non-small cell lung cancer (NSCLC), small cell lung cancer (SCLC) and colorectal cancer (CRC) comprising the steps of: providing a blood plasma sample from the patient collected at a first time point during treatment regimen; providing a blood plasma sample from the patient collected at a second time point during treatment regimen; determining in the samples the sequence of at least a portion of each of the biomarkers listed in Table 1 or Table 2; determining in the samples the ratio of the number of mutations detected in the biomarkers to the volume of the samples (MMPM); and continuing the therapy regimen if the MMPM in the second sample is lower than in the first sample; or altering the therapy regimen if the MMPM in the second sample is not lower than in the first sample. Altering the therapy regimen may comprise one or more of increasing the dose of therapy, adding one or more therapeutic agents, and extending the duration of therapy as compared to the non-altered therapy regimen.

In one embodiment, the invention is a computer system designed to implement an algorithm for whether a cancer patient has positively responded to a therapy regimen, wherein the algorithm analyses sequencing data on one or more biomarkers obtained from at least two patient's blood samples collected at separate time points during the therapy regimen, the algorithm containing one or more steps selected from mutation detection, error correction, counting the number of mutations per sample and determining the ratio of the number of mutations in a sample to the sample volume (MMPM), determining whether MMPM has decreased at subsequent time points and reporting that the patient has responded to therapy if MMPM has decreased between subsequent time points and reporting that the patient has not responded to therapy if MMPM has not decreased between subsequent time points.

In one embodiment, the invention is a computer system designed to implement an algorithm for selecting a therapy for a cancer patient wherein the algorithm analyses sequencing data on one or more biomarkers obtained from at least two patient's blood samples collected at separate time points during the therapy regimen, the algorithm containing one or more steps selected from mutation detection, error correction, counting the number of mutations per sample and determining the ratio of the number of mutations in a sample to the sample volume (MMPM), determining whether MMPM has decreased at subsequent time points and reporting suggested selection of the same therapy if MMPM has decreased between subsequent time points and reporting suggested selection of an alternative therapy if MMPM has not decreased between subsequent time points.

DETAILED DESCRIPTION OF THE INVENTION

Definitions

Figure 1:
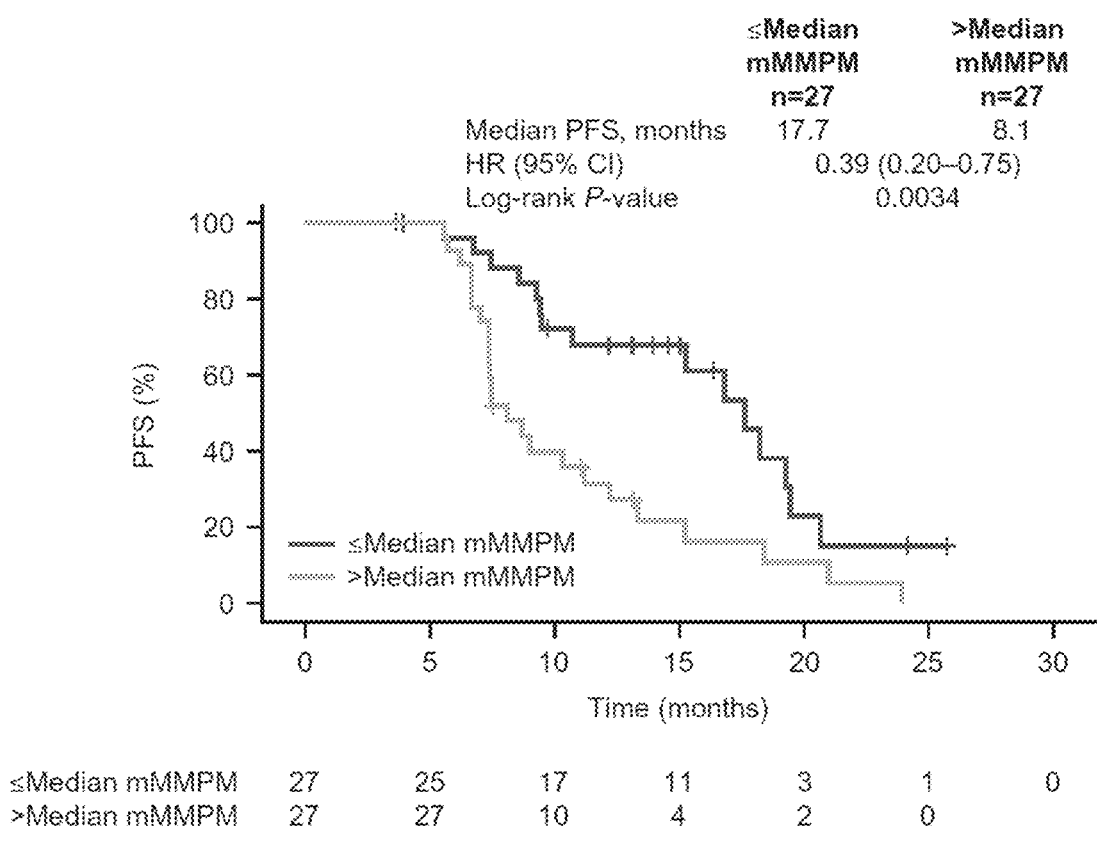
FIG. 1 is a Kaplan-Meier graph comparing progression free survival (PFS) of mCRC patients with MMPM measured below the median to those with MMPM above or equal to the median.

The following definitions are not limiting but merely aid in understanding this disclosure.

The term "PFS" is used herein to describe the time of Progression Free Survival for a patient.

The term "OS" is used herein to describe the time of Overall Survival for a patient.

The term "circulating tumor DNA (ctDNA)" is used herein to describe a portion of cell-free DNA (cfDNA) found in human blood plasma or serum that originates from the tumor. Circulating tumor DNA is distinguished from non-tumor DNA by the mutations characteristic of the tumor.

The term "biomarker" is used herein to describe a nucleotide sequence that contains information relevant to the biological or clinical phenomenon. For example, the information may be a mutation status of the nucleotide sequence. The biomarker can be a gene (including coding sequence, regulatory sequence, intron or a splice site) or an intergenic region. The clinical phenomenon can be the presence of malignant cells, e.g., tumor cells in a patient's sample.

The term "whole genome sequencing of WGS" is used herein to describe sequencing of the entire genome of a cell or organism from which a cells or cells are derived. The term "whole exome sequencing of WES" is used herein to describe sequencing of all the exons present in all the genes of the genome. Both WGS and WES on human or other higher order vertebrate genomes are performed using massively parallel sequencing methods (next generation sequencing methods) capable of gathering and storing large amounts of sequence information.

The invention describes methods of treatment of a tumor patient, a method of monitoring the treatment of a tumor patient and a method of modifying or altering a treatment regimen of a tumor patient. In some embodiments, the tumor is selected from non-small cell lung cancer (NSCLC), small cell lung cancer (SCLC) and colorectal cancer (CRC).

Tumor cell are known to accumulate somatic mutations during tumor development and progression. Various methods of assessing tumor mutations have been used for diagnosis and therapy selection. For example, Tumor Mutation Burden (TMB), defined as a number of mutations in a tumor sample from a patient is a predictive biomarker for chemotherapies and cancer immunotherapies for an array of solid metastatic malignancies. TMB is often measured by whole exome sequencing (WES) or by sequencing of multi-megabase panels. In recent studies, a panel comprising 1.2 megabase of the genome was analyzed for mutations. Hybridization capture of exonic regions from 185, 236, 315, or 405 cancer-related genes and select introns from 19, 28, or 31 genes commonly rearranged in cancer was applied to ≥50 ng of DNA extracted from formalin-fixed, paraffin-embedded clinical cancer specimens. Chalmers et al. (2017) *Analysis of* 100,000 *human cancer genomes reveals the landscape of tumor mutational burden*, Genome Medicine (2017) 9:34, Goodman et al., (2017) *Tumor Mutational Burden as an Independent Predictor of Response to Immunotherapy in Diverse Cancers*, doi: 10.1158/1535-7163.MCT-17-0386, Maia, M. C., et al., (2018) *Relationship of tumor mutational burden (TMB) to immunotherapy response in metastatic renal cell carcinoma (mRCC)*, Journal of Clinical Oncology 36, no. 6_suppl (Feb. 20, 2018) 662-662. Recently, a new more practical, non-invasive method of assessing tumor-characteristic mutations has been developed and described in a U.S. Provisional Application Ser. No. 62/666,329 filed on May 3, 2018 titled "*Surrogate Marker and Method for Tumor Mutation Burden Measurement*". Instead of whole genome analysis such as WGS or WES, the new method utilizes a small targeted sequencing panel to measure mutations found in circulating tumor DNA (ctDNA) of cancer patients. The method employs greater depth of sequencing compared to e.g., tissue-based sequencing and utilizes a smaller targeted sequencing panel that enriches the commonly mutated genes in solid tumors. The mutation count is assessed using the AVENIO ctDNA Surveillance Kit (Roche Sequencing Solutions, Inc., Pleasanton, Cal.), a targeted next-generation sequencing panel of only 198 kilobases. The panel was designed to maximize the number of relevant mutations to be detected in lung and colorectal cancers by interrogating only a small portion of the human genome. Although a smaller portion of the genome is sequenced and the samples include only cell-free DNA, the methods has been shown to adequately assess mutations present in tumor DNA.

The present invention utilizes the same limited genomic panel approach. The invention is a method of assessing and treating a patient with a tumor wherein the effectiveness of the treatment regimen is monitored by detecting a change in tumor mutations. The novel method is economical and non-invasive. More specifically, the effectiveness of a therapy regimen is monitored by detecting changes in a novel parameter: mutant molecules per milliliter-of-plasma (MMPM). MMPM is a measure of the number of tumor mutations detected divided by the volume of plasma from which the tested nucleic acid has been extracted. One of skill in the art would realize that the sample need not be measured in milliliters to determine MMPM. Any other measurement of the amount of sample, e.g., mass or volume determined in any units is equally suitable for detecting and monitoring MMPM. The invention further comprises determining the change in MMPM with treatment. Blood samples are collected from the patient at various points during treatment including optionally a pretreatment measurement and one or more additional measurement. MMPM values are compared between the different time points. The method of treatment further comprises continuing with the treatment regimen if a reduction in MMPM is observed between time points. The method of treatment alternatively comprises a step of altering the treatment regimen if no reduction in MMPM is observed between time points.

In some embodiments, the invention uses a biomarker panel to identify tumor-specific somatic mutations by next-generation sequencing (NGS). In some embodiments, the invention utilizes a blood or blood-derived sample from a patient. The sample can include any fraction of blood, e.g., serum or plasma, which contains cell-free DNA including circulating tumor DNA (cfDNA or ctDNA). In some embodiments, the sample is taken serially at various times during treatment, e.g., before during and after a chemotherapy or chemora-diotherapy regimen. The blood sample from the is collected and preserved by any suitable means that preserves the cell free DNA therein including collecting the blood sample in a preservative medium, e.g., such as described in application Ser. No. 12/689,370 Preservation of fetal nucleic acids in maternal plasma, filed on Jan. 19, 2010.

In some embodiments, the invention utilizes a biomarker panel, including a gene panel or a mutation panel or a somatic variant panel. The mutations may include single-nucleotide variations (SNVs), deletions and insertions (in-dels) that correspond to on-sense missense and frame-shift mutations if they occur in the coding regions of genes. Other types of mutations include gene fusions and translocations. The selection, size and content of such panels has been described e.g., in U.S. patent applications Ser. Nos. 14/209, 807, 14/774,518 and International app. No. PCT/US2015/ 049838 titled "Identification and Use of Circulating Tumor Markers." In some embodiments, the invention includes determining the sequence of the biomarkers in the panel, e.g., the genes listed in Table 1 or Table 2. In some embodiments, the entire sequence of a gene is determined. In other embodiments, the entire coding sequence of a gene is determined. In other embodiments, only the sequence of a portion of the gene known to undergo mutagenesis in cancer is determined. In yet other embodiments, the bio-marker is not associated with a coding sequence but is associated with a regulatory sequence or a sequence of unknown function but known to be consistently mutated in human tumors. In some embodiments, the portion of the gene or other sequence is selected for inclusion in the panel if it is characterized by recurrence of the mutation in multiple patients afflicted with the same type of tumor or different types of tumors. Other criteria for inclusion in the panel are disclosed in the patent application "Identification and Use of Circulating Tumor Markers" supra.

In the context of the present invention, the sequence of a biomarker can be determined via any suitable method known in the art. The suitable method would have sufficient accuracy, e.g., sensitivity and specificity to detect rare mutant sequences co-occurring with non-mutant sequences. In some embodiments, the sequencing method includes an error correction step, such as use of molecular barcodes, error stereotyping and other chemical or computation meth-ods of error suppression as described e.g., in see the patent applications "Identification and Use of Circulating Tumor Markers", supra. The sequencing method may include a massively parallel sequencing method, including an array based sequencing (Illumina, San Diego, Cal.), an emulsion-based sequencing (ThermoFisher, Waltham, Mass.) an opti-cal measurement based sequencing (Pacific BioSciences, Menlo Park, Cal.) or a nanopore-based sequencing (Oxford Naopore, Oxford, UK or Roche Sequencing Solutions, Santa Clara, Cal.).

The sequence data is compared to a reference genome sequence to determine mutations. In some embodiments, the reference sequence is the canonical human genome assem-bly e.g., HG38. Changes in the nucleic acid sequence compared to the reference genome are identified and scored as mutations. In some embodiments, one or more filters are applied to select mutations to be scored. In some embodi-ments, only mutations in the coding regions are scored. In some embodiments, only non-synonymous mutations in the coding regions are scored. In other embodiments, both non-synonymous and synonymous mutations in the coding regions are scored. In yet other embodiments, to enable detection of lower frequency mutation events, mutations in the cancer driver genes are excluded from scoring.

In some embodiments, the invention includes a step of assessing the status of a cancer in a patient receiving therapy by determining the duration of one or more of progression free survival (PFS), recurrence free survival (RFS), total time to recurrence (TTR) and overall survival (OS). The assessing is based on the change in MMPM during treatment determined as described herein.

In some embodiments, the invention provides methods for identifying cancer patients that are responding favorably to the treatment regimen being administered. The invention also provides methods for identifying cancer patients that are not responding favorably to treatment regimen being administered. Specifically, the invention is a method of treatment of a cancer patient comprising the steps of at more than one time point during the treatment, isolating nucleic acids from a cell-free blood sample obtained from the patient, in the isolated nucleic acid, determining the sequence of at least a portion of each of the biomarkers listed in Table 1 or in Table 2, comparing the sequence to the reference sequence and identifying mutations, determining MMPM as a ratio of the number of mutations identified and the amount (e.g., volume) of blood or plasma collected and determining the change in MMPM between the time points. The method further comprises continuing the therapy regi-men if MMPM has decreased between the subsequent time points and altering the therapy regimen if MMPM has not decreased between the subsequent time points. In some embodiments, the therapy regimen for colorectal cancer (CRC) including metastatic colorectal cancer (mCRC) is selected from bevacizumab (BEV) plus 5-fluorouracil/leu-covorin/oxaliplatin (FOLFOX) and 5-fluorouracil/leuco-vorin/irinotecan (FOLFIRI), administered concurrently (cFOLFOXIRI-BEV), or capecitabine plus bevacizumab. In some embodiments, progression therapy for mCRC is selected bevacizumab and a fluoropyrimidine-based chemo-therapy.

One aspect of the invention includes a system for detect-ing MMPM in a patient. The system comprises a processor and a non-transitory computer readable medium coupled to the processor, the medium comprising code executable by the processor for performing a method comprising the steps of analyzing sequencing data on biomarkers from Table 1 or Table 2 obtained from sample collected at more than one time point during treatment, performing sequence compari-son and mutation detection, error correction, determining MMPM as a ratio of the number of mutations identified and the amount (e.g., volume) of plasma and determining whether MMPM has decreased between subsequent time points.

In some embodiments, the computer readable medium, which may include one or more storages devices, comprises a database including a listing of available therapies depend-ing on the dynamics of MMPM measurements in the patient. The computer readable medium further comprises a program code having instructions to generate a report listing suitable therapies. The system may comprise various functional aspects such a server including a processor for processing digital data, a memory coupled to the processor for storing digital data, an input digitizer coupled to the processor for inputting digital data, program code stored in the memory and accessible by the processor, a display device coupled to the processor and memory for displaying information derived from digital data, data networking, and one or more informational databases. The databases may include patient data, patient sample data, clinical data including prior treatment data, a list of therapies and therapeutic agents, patient tracking data and the like.

In some embodiments, the invention utilizes a biomarker panel, such as AVENIO® ctDNA Analysis Kit (Roche Sequencing Solutions, Inc., Pleasanton, Cal.) that is capable of analyzing the tissue and blood of patients to identify and quantify tumor specific mutations in the samples. The composition of the biomarker panel in AVENIO® ctDNA Analysis Kit (expanded panel) is shown in Table 1. The composition of the biomarker panel in AVENIO® ctDNA Analysis Kit (surveillance panel) is shown in Table 2.

TABLE 1

| Composition of the expanded biomarker panel | | | | | |
|---|---|---|---|---|---|
| APC | KRAS | ABL1 | FGFR3 | JAK3 | RAF1 |
| BRCA1 | MET | AKT1 | FLT1 | KDR | RNF43 |
| BRCA2 | TP53 | AKT2 | FLT3 | MAP2K1 | TERT promoter |
| EGFR | KIT | ARAF | FLT4 | MAP2K2 | TSC1 |
| ERBB2 | NRAS | CDK6 | GATA3 | MTOR | TSC2 |
| ALK | PDGFRA | CSF1R | GNA11 | NFE2L2 | PTEN |
| BRAF | RET | CTNNB1 | GNAQ | NTRK1 | RB1 |
| DPYD | ROS1 | DDR2 | GNAS | PDGFRB | SMAD4 |
| AR | MSH2 | EZH2 | IDH1 | PIK3CA | SMO |
| CCND1 | MSH6 | FGFR1 | IDH2 | PIK3R1 | STK11 |
| CCND2 | NF2 | FGFR2 | JAK2 | PTCH1 | VHL |
| CCND3 | PDCD1LG2 | CDK4 | ESR1 | KEAP1 | UGT1A1 |
| CD274 | PMS2 | CDKN2A | FBXW7 | MLH1 | |

TABLE 2

| Composition of the surveillance biomarker panel | | | | | | |
|---|---|---|---|---|---|---|
| ABCC5 | CSMD1 | FAT1 | HTR1E | MAP7D3 | PIK3CA | SV2A |
| ABCG2 | CSMD3 | FBN2 | HTR2C | MKRN3 | PIK3CG | T |
| ACTN2 | CTNNB1 | FBXL7 | IFI16 | MMP16 | PKHD1L1 | THSD7A |
| ADAMTS12 | CTNND2 | FBXW7 | IL7R | MTX1 | POLE | TIAM1 |
| ADAMTS16 | CYBB | FCRL5 | INSL3 | MYH7 | POM121L12 | TMEM200A |
| ARFGEF1 | DCAF12L1 | FOXG1 | ITGA10 | MYT1L | PREXI | TNFRSF21 |
| ASTN1 | DCAF12L2 | FRYL | ITSN1 | NAV3 | PTPLA | TNN |
| ASTN2 | DCAF4L2 | GBA3 | KCNA5 | NEUROD4 | RALYL | TNR |
| AVPR1A | DCLK1 | GBP7 | KCNB2 | NFE2L2 | RFX5 | TRHDE |
| BCHE | DCSTAMP | GJA8 | KCNC2 | NLGN4X | RIN3 | TRIM58 |
| BPIFB4 | DDI1 | GPR139 | KCNJ3 | NLRP3 | RNASE3 | TRPS1 |
| C6 | DLGAP2 | GRIA2 | KCTD8 | NMUR1 | ROBO2 | UGT3A2 |
| C6orf118 | DMD | GRIK3 | KEAP1 | NOL4 | SEMA5B | USH2A |
| CA10 | DNTTIP1 | GRIN2B | KIAA1211 | NPAP1 | SLC18A3 | USP29 |
| CACNA1E | DOCK3 | GRIN3B | KIF17 | NR0B1 | SLC39A12 | VPS13B |
| CDH12 | DSC3 | GRM1 | KIF19 | NRXN1 | SLC6A5 | WBSCR17 |
| CDH18 | DSCAM | GRM5 | KLHL31 | NXPH4 | SLC8A1 | WIPF1 |
| CDH8 | EGFLAM | GRM8 | KPRP | NYAP2 | SLITRK1 | WSCD2 |
| CDH9 | EPHA5 | GSX1 | LPPR4 | OPRD1 | SLITRK4 | ZC3H12A |
| CDKN2A | EPHA6 | HCN1 | LRFN5 | P2RY10 | SLITRK5 | ZFPM2 |
| CHRM2 | EYS | HCRTR2 | LRP1B | PAX6 | SLPI | ZIC1 |
| CNTN5 | FAM135B | HEBP1 | LRRC7 | PCDH15 | SMAD4 | ZIC4 |
| CNTNAP2 | FAM151A | HECW1 | LRRTM1 | PDYN | SOX9 | ZNF521 |
| CPXCR1 | FAM5B | HS3ST4 | LRRTM4 | PDZRN3 | SPTA1 | ZSCAN1 |
| CPZ | FAM5C | HS3ST5 | LTBP4 | PGK2 | ST6GALNAC3 | KIT |
| CRMP1 | FAM71B | HTR1A | MAP2 | PHACTR1 | STK11 | NRAS |
| APC | KRAS | ALK | PDGFRA | MET | BRAF | RET |
| BRCA1 | BRCA2 | TP53 | DPYD | EGFR | ERBB2 | UGT1A1 |

In some embodiments, some or all genes from the panel of 77 genes listed in Table 1 is used. In some embodiments, some or all genes from the the panel of 197 genes listed in Table 2 is used. The mutation (MMPM) measurements are taken at one or more points during the treatment regimen to assess changes in MMPM. In some embodiments, the initial measurement is taken before commencement of the treatment regimen. In some embodiments, the final measurement is taken after completion of the treatment regimen. In some embodiments, no pre-treatment MMPM measurement is available and mutation (MMPM) measurements are taken only during and optionally post-treatment to assess changes in MMPM.

EXAMPLES

Example 1. Using MMPM to Determine Whether Lung Cancer (NSCLC) Patients have Responded to Therapy Blood plasma samples were collected from a cohort of advanced non-small cell lung cancer (NSCLC) adenocarcinoma patients. The AVENIO® ctDNA kit, Surveillance Panel (Roche Sequencing Solutions, Pleasanton, Cal.) was used to assess the number of mutations in patient samples. Cell-free DNA (cfDNA) from the patients was isolated and analyzed according to the manufacturer's instructions of the AVENIO® ctDNA Kit. Post-treatment MMPM values were compared with the MMPM value at baseline and/or the previous treatment time point. At baseline (b0), we identified variants in all patients to enable ctDNA monitoring. We define the plasma draw after the first and second treatment cycle as p1, and p2, respectively.

By applying the Continuous Responder algorithm, defined by a continuous drop in ctDNA levels represented by mean MMPM reduction over time (p2<p1<b0), to a mean MMPM below 8 at p2. As a result, continuous responders 13/43 (30%) were associated with a better therapy response indicated by PFS (P=0.028 HR 0.45; 95% CI 0.23-0.90) and OS (P=0.0074 HR 0.3; 95% CI 0.12-0.77). The continuous responders demonstrated a median overall survival benefit of 11.25 months over the poor responders. The results demonstrate that early post-treatment ctDNA level measured by NGS was associated with chemoradiation therapy response in advanced lung adenocarcinoma population.

Example 2. Using MMPM to Determine Whether
Lung Cancer (SCLC) Patients have Responded to
Therapy From the prospective, observational German Lung Cancer
Multi-Marker Study we selected the first 72 consecutive
small-cell lung cancer (SCLC) patients, UICC-stage IIIB/IV,
where plasma samples were available prior to start of
therapy, and prior to the second cycle of chemotherapy, and
prior to third cycle. We hypothesized that assessment of the
level of ctDNA after starting therapy relates to treatment
effect and prognosis. We employed AVENIO ctDNA Sur-
veillance Kit (Roche Sequencing Solutions, Pleasanton,
Cal.), a 197-gene NGS assay, which allowed us to perform
longitudinal ctDNA analysis and measure the mutant mol-
ecules per milliliter-of-plasma (MMPM), which quantifies
ctDNA over all variants of all sequenced genomic regions.
All extracted cfDNA samples were processed and sequenced
in order of date of blood draw. At baseline (b0), we identified
variants in all (72/72) subjects to enable ctDNA monitoring.
Using serial liquid biopsies from each subject, the mean
MMPM at post-first treatment cycle (p1) and the mean
MMPM at post-second treatment cycle (p2) were analyzed.
We tested a Continuous Responder algorithm, defined by a
continuous drop in ctDNA levels represented by mean
MMPM reduction over time (p2<p1<b0), to a mean MMPM
below 18 at p2. As a result, continuous responders 47/72
were associated with a better therapy response OS HR=2
(P=0.0092%; CI 1.2-3.4). The continuous responders dem-
onstrated a median survival benefit of 4.6 months over the
poor responders. Neither gender, nor age, nor ECOG, nor
stage were predictors of response in the models. The results
demonstrate that an early assessment of treatment effect can
be measured by mutant molecule counts in the plasma. A
decrease in post-treatment ctDNA levels was associated with
better prognosis in advanced SCLC.

Example 3. Disease Monitoring in Metastatic
Colorectal Cancer (mCRC) Patients Using MMPM Patient Selection and Treatment The patients selected for the study were phase 2 study of
patients with previously untreated mCRC. After a 21-day
screening period, patients were randomized 1:1:1 to a
4-month treatment induction phase with cFOLFOXIRI-
BEV, sFOLFOXIRI-BEV, or FOLFOX-BEV, administered
in two-week cycles. Induction could be extended up to an
additional 2 months at the discretion of the treating physi-
cian. Induction therapy was followed by maintenance with
5-fluorouracil, leucovorin, and bevacizumab every 2 weeks
or capecitabine plus bevacizumab every 3 weeks. Following
disease progression, patients were to receive second-line
bevacizumab and a fluoropyrimidine-based chemotherapy
of the investigator's choice. Treatment continued until pro-
gression, death, withdrawal of consent, or unacceptable
toxicity. Treatment efficacy was assessed by site investiga-
tors per Response Evaluation Criteria in Solid Tumors
(RECIST) v1.1 during the pre-randomization screening
period and every 8 weeks thereafter. PFS was calculated as
the time from randomization to first disease progression or
death from any cause, whichever occurred earlier. Patients
without an event were censored at their last tumor assess-
ment.

Tissue and Plasma Collection for Biomarker
Analysis

Biomarker-evaluable patients were defined as those who
provided optional consent to participate in the biomarker program and who had one tissue sample, one pre-induction
plasma sample, and one post-induction plasma sample.
Tissue and pre-induction plasma samples had to be analyz-
able and collected within 90 days of each other. In addition,
post-induction plasma samples had to be collected within 60
days of last drug induction date. Archival or fresh baseline
(cycle 1, day 1, pre-treatment) tumor tissue for each patient
was collected. Blood plasma for biomarker analysis was
collected at baseline and at the end of the induction phase
(end of cycle 8, with possible extension to cycle 12, per the
discretion of the investigator).

Biomarker Assessment of Tumor DNA and Plasma
ctDNA cfDNA was extracted from 4 mL of plasma using the cobas'
cfDNA Sample Preparation kit (Roche Molecular Systems,
Pleasanton, Cal.), and tumor DNA was isolated from for-
malin-fixed paraffin embedded (FFPE) tumor tissue sections
using the cobas' DNA Sample Preparation kit (Roche
Molecular Systems, Pleasanton, Cal.). DNA yields were
quantified by a Qubit HS assay (ThermoFisher, Waltham,
Mass). cfDNA samples were prepared for sequencing using
the AVENIO ctDNA Expanded Kit (Research Use Only;
Roche Sequencing Solutions, Pleasanton, Cal.) using 1 to
208 ng (median 50 ng) of cfDNA. DNAs sequencing was
performed on an Illumina HiSeq 4000. ctDNA variants were
identified using the AVENIO ctDNA Analysis Software
(Roche Sequencing Solutions, Pleasanton, Cal.)

Determining Mutant Molecules Per Milliliter
(MMPM)

Allele Frequency (AF) for a given somatic mutation was
calculated as the number of de-duplicated reads with that
mutation divided by the total number of de-duplicated reads
covering that genomic position. MMPM for a given somatic
mutation was calculated from the AF of that variant by
multiplying by the extracted mass (ng), dividing by the
plasma volume (mL), and adjusting by a factor of 330
haploid human genome equivalents (hGE) per 1 ng. The
mean AF or mean MMPM for each plasma sample was
calculated across somatic variants (single nucleotide vari-
ants and indels) pre-defined by the matched tissue sample.
Cutoffs for classifiers were determined based on distribution
of post-induction mean AF and mean MMPM values. Fol-
lowing testing of multiple cutoff values, we found that mean
MMPM value of 8 MM/mL showed clinically significant
separation of good vs. poor molecular responders.

Statistical Methods

Kaplan-Meier method and log-rank tests were used to esti-
mate the median PFS and log-rank p-value. Cox propor-
tional hazards models were used to estimate the hazard ratio
(HR) and associated 95% CIs.

Results

Of the 54 patients in the biomarker evaluable population, 6
patients had curative surgery (i.e., surgery with an outcome
of R0 resection) while on study. Median follow-up duration
was 19.3 (range, 6.7-28.0) months in the 54 patients
included in the biomarker evaluable population. Median
PFS after first-line induction therapy in the biomarker evalu-
able population (n=54) was similar to median PFS observed in the remaining STEAM population (n=226) (11.2 vs 10.9 months, respectively; HR 1.09 [95% CI 0.77-1.54], log-rank P=0.6361).

Association of Post-Induction Mean MMPM (mMMPM) with PFS

Figure 2:
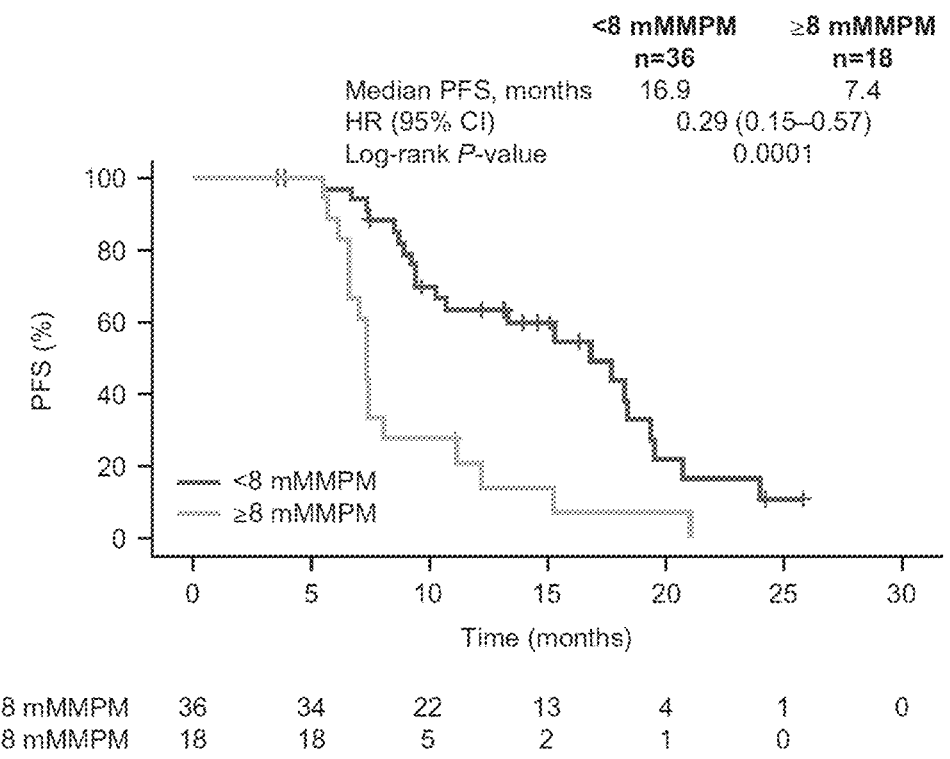
FIG. 2 is a Kaplan-Meier graph comparing progression free survival (PFS) of mCRC patients with MMPM<8 and ≥8.

As an alternative method of estimating ctDNA levels in plasma, we evaluated a novel parameter: absolute variant molecules per unit plasma, (MMPM). We determined association of changes in MMPM with PFS. Post-induction mean MMPM (mMMPM) levels were inversely associated with PFS regardless of cutoff used (median, 8 MM/mL, or 10 MM/mL), suggesting that mMMPM levels are also prognostic for clinical outcomes. In patients with ≤median vs ≥median mMMPM, median PFS was 17.7 vs 8.1 months, respectively, and HR was 0.39 (95% CI 0.20-0.75) (log-rank P=0.0034). (FIG. 1). In patients with <8 MM/mL vs≥8 MM/mL, median PFS was 16.9 vs 7.4 months, respectively, and HR was 0.29 (95% CI 0.15-0.57, log-rank P=0.0001). (FIG. 2).

While mAF and mMMPM generally correlated with each other, three patients in this analysis with very high (>100 ng/mL) plasma cfDNA levels had low post-induction mAF levels (0.21%, 0.36%, and 0.03%) but greater than median mMMPM (211.62, 793.43, 10.93, respectively). Two of the three patients had relatively short PFS durations (6.7 and 7.5 months). In these outlier cases, mMMPM was a better prognostic biomarker than mAF, as mAF may have underestimated disease burden.

We claim:

1. A method of treatment of colorectal cancer (CRC) comprising the steps of:

(a) providing a blood plasma sample from a CRC patient collected at a first time point during a therapy regimen;

(b) providing a blood plasma sample from the patient collected at a second time point during the therapy regimen;

(c) sequencing from the sample at least a portion of each of the biomarkers listed in Table 1 or Table 2 wherein Table 1 is:

| | | | | | |
|---|---|---|---|---|---|
| APC | KRAS | ABL1 | FGFR3 | JAK3 | RAF1 |
| BRCA1 | MET | AKT1 | FLT1 | KDR | RNF43 |
| BRCA2 | TP53 | AKT2 | FLT3 | MAP2K1 | TERT promoter |
| EGFR | KIT | ARAF | FLT4 | MAP2K2 | TSC1 |
| ERBB2 | NRAS | CDK6 | GATA3 | MTOR | TSC2 |
| ALK | PDGFRA | CSF1R | GNA11 | NFE2L2 | PTEN |
| BRAF | RET | CTNNB1 | GNAQ | NTRK1 | RB1 |
| DPYD | ROS1 | DDR2 | GNAS | PDGFRB | SMAD4 |
| AR | MSH2 | EZH2 | IDH1 | PIK3CA | SMO |
| CCND1 | MSH6 | FGFR1 | IDH2 | PIK3R1 | STK11 |
| CCND2 | NF2 | FGFR2 | JAK2 | PTCH1 | VHL |
| CCND3 | PDCD1LG2 | CDK4 | ESR1 | KEAP1 | UGT1A1 |
| CD274 | PMS2 | CDKN2A | FBXW7 | MLH1 | | and Table 2 is:

| | | | | | | |
|---|---|---|---|---|---|---|
| ABCC5 | CSMD1 | FAT1 | HTR1E | MAP7D3 | PIK3CA | SV2A |
| ABCG2 | CSMD3 | FBN2 | HTR2C | MKRN3 | PIK3CG | T |
| ACTN2 | CTNNB1 | FBXL7 | IFI16 | MMP16 | PKHD1L1 | THSD7A |
| ADAMTS12 | CTNND2 | FBXW7 | IL7R | MTX1 | POLE | TIAM1 |
| ADAMTS16 | CYBB | FCRL5 | INSL3 | MYH7 | POM121L12 | TMEM200A |
| ARFGEF1 | DCAF12L1 | FOXG1 | ITGA10 | MYT1L | PREX1 | TNFRSF21 |
| ASTN1 | DCAF12L2 | FRYL | ITSN1 | NAV3 | PTPLA | TNN |
| ASTN2 | DCAF4L2 | GBA3 | KCNA5 | NEUROD4 | RALYL | TNR |
| AVPR1A | DCLK1 | GBP7 | KCNB2 | NFE2L2 | RFX5 | TRHDE |
| BCHE | DCSTAMP | GJA8 | KCNC2 | NLGN4X | RIN3 | TRIM58 |
| BPIFB4 | DDII | GPR139 | KCNJ3 | NLRP3 | RNASE3 | TRPS1 |
| C6 | DLGAP2 | GRIA2 | KCTD8 | NMUR1 | ROBO2 | UGT3A2 |
| C6orf118 | DMD | GRIK3 | KEAP1 | NOL4 | SEMA5B | USH2A |
| CA10 | DNTTIP1 | GRIN2B | KIAA1211 | NPAP1 | SLC18A3 | USP29 |
| CACNA1E | DOCK3 | GRIN3B | KIF17 | NROB1 | SLC39A12 | VPS13B |
| CDH12 | DSC3 | GRM1 | KIF19 | NRXN1 | SLC6A5 | WBSCR17 |
| CDH18 | DSCAM | GRM5 | KLHL31 | NXPH4 | SLC8A1 | WIPF1 |
| CDH8 | EGFLAM | GRM8 | KPRP | NYAP2 | SLITRK1 | WSCD2 |
| CDH9 | EPHA5 | GSX1 | LPPR4 | OPRD1 | SLITRK4 | ZC3H12A |
| CDKN2A | EPHA6 | HCN1 | LRFN5 | P2RY10 | SLITRK5 | ZFPM2 |
| CHRM2 | EYS | HCRTR2 | LRP1B | PAX6 | SLPI | ZIC1 |
| CNTN5 | FAM135B | HEBP1 | LRRC7 | PCDH15 | SMAD4 | ZIC4 |
| CNTNAP2 | FAM151A | HECW1 | LRRTM1 | PDYN | SOX9 | ZNF521 |
| CPXCR1 | FAM5B | HS3ST4 | LRRTM4 | PDZRN3 | SPTA1 | ZSCAN1 |
| CPZ | FAM5C | HS3ST5 | LTBP4 | PGK2 | ST6GALNAC3 | KIT |
| CRMP1 | FAM71B | HTR1A | MAP2 | PHACTR1 | STK11 | NRAS |
| APC | KRAS | ALK | PDGFRA | MET | BRAF | RET |
| BRCA1 | BRCA2 | TP53 | DPYD | EGFR | ERBB2 | UGT1A1; |

(d) calculating the ratio of the number of mutations detected in the biomarkers to the volume of the samples (MMPM);

(e) continuing the therapy regimen if the MMPM in the second sample is lower than in the first sample; or (f) altering the therapy regimen if the MMPM in the second sample is not lower than in the first sample, wherein altering the therapy regimen comprises one or more of increasing the dose of therapy, adding one or more therapeutic agents, and extending the duration of therapy as compared to the non-altered therapy regimen, wherein the therapy regimen is selected from treatment with FOLFOXIRI-bevacizumab, treatment with FOLFOX-bevacizumab, capecitabine-bevacizumab and chemoradiation therapy.

* * * * *